United States Patent [19]

Saito

[11] Patent Number: 5,682,414
[45] Date of Patent: Oct. 28, 1997

[54] X-RAY COMPUTERIZED TOMOGRAPHY APPARATUS

[75] Inventor: Yasuo Saito, Tochigi-ken, Japan

[73] Assignee: Kabushiki Kaisha Toshiba, Kawasaki, Japan

[21] Appl. No.: 622,316

[22] Filed: Mar. 26, 1996

Related U.S. Application Data

[60] Division of Ser. No. 352,087, Nov. 30, 1994, Pat. No. 5,541,971, which is a continuation-in-part of Ser. No. 286,423, Aug. 5, 1994, abandoned.

[30] Foreign Application Priority Data

Sep. 6, 1993 [JP] Japan ................................ 5-220918
Sep. 5, 1994 [JP] Japan ................................ 6-211046

[51] Int. Cl.⁶ ................................................ G21K 51/10
[52] U.S. Cl. .................................... 378/146; 378/901
[58] Field of Search ............................. 378/4, 15, 19, 378/20, 146, 901

[56] References Cited

U.S. PATENT DOCUMENTS

| | | | |
|---|---|---|---|
| 5,212,717 | 5/1993 | Hada | 378/4 |
| 5,430,783 | 7/1995 | Hu et al. | 378/4 |
| 5,454,010 | 9/1995 | Migita et al. | |

FOREIGN PATENT DOCUMENTS 5-184563  7/1993  Japan.

Primary Examiner—Don Wong
Attorney, Agent, or Firm—Finnegan, Henderson, Farabow, Garrett & Dunner, L.L.P.

[57] ABSTRACT

An X-ray computerized tomography apparatus includes n number of X-ray detector arrays. Each of X-ray signals detected by the detector arrays during helical scan is stored associated with an angle of a rotating gantry and the position of a top board. Also, each of the X-ray signals is stored associated with an angle differing by 180 degrees and the corresponding position of the top board. A pair of first and second X-ray signals for the same angle of the gantry is selected for each of predetermined angles ranging from 0° to 360°. The first X-ray signal corresponding to the first position closest to the position of a plane section of a subject under examination and the second X-ray signal corresponding to the second position that is closest to the position of the plane section on the opposite side of the first position for the first X-ray signal with respect to the position of the plane section are subjected to weighted-averaging according to their distance from the position of the plane section. A tomogram of the plane section is reconstructed from the results of the weighted-averaging.

18 Claims, 10 Drawing Sheets

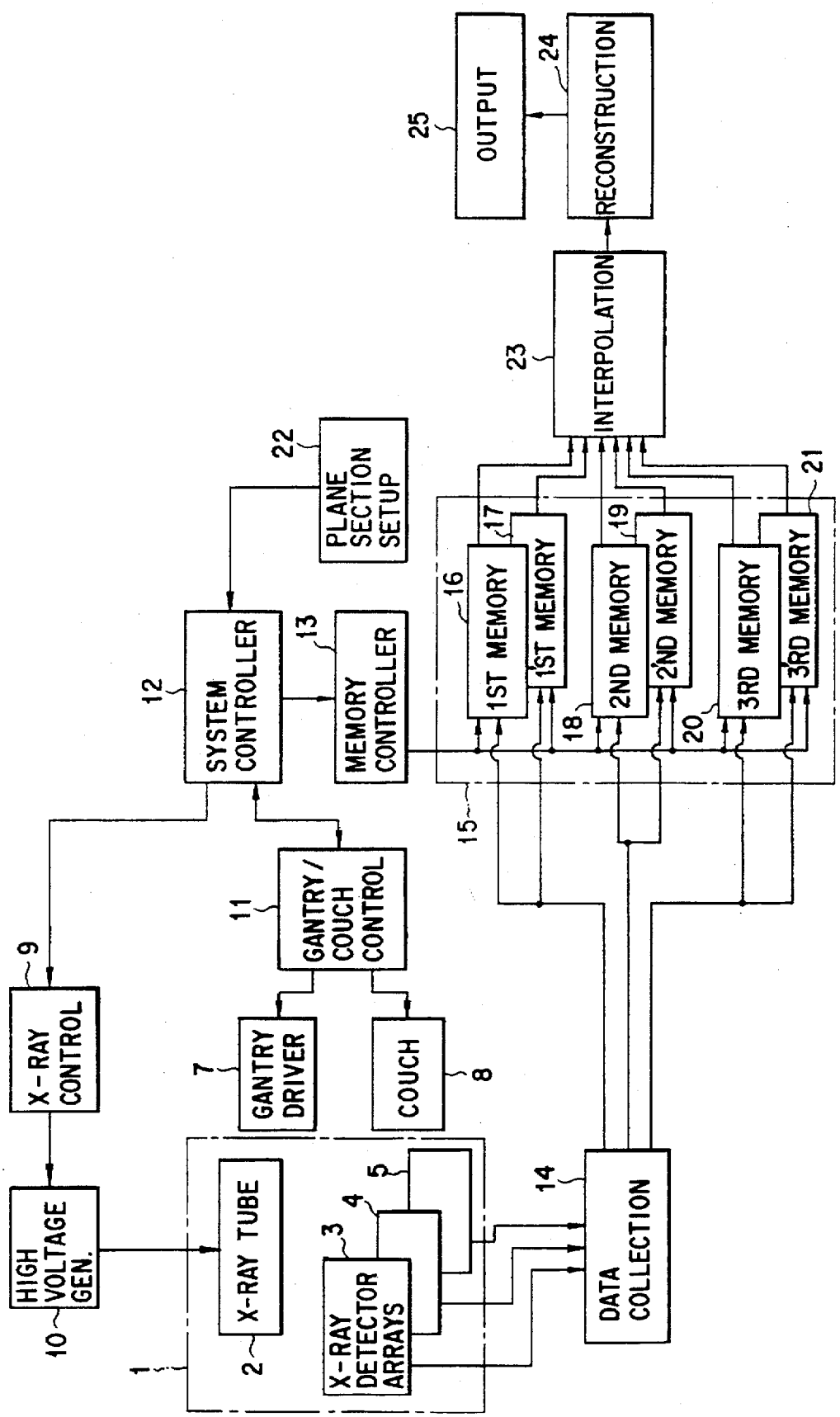
F I G. 1

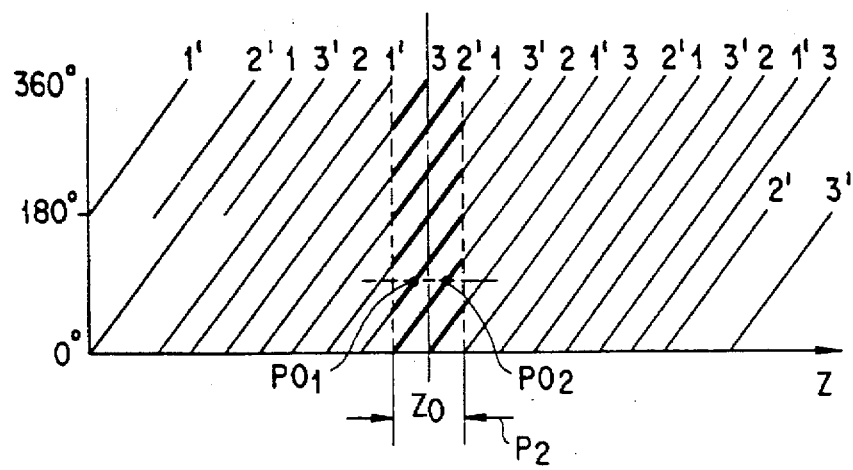
F I G. 5
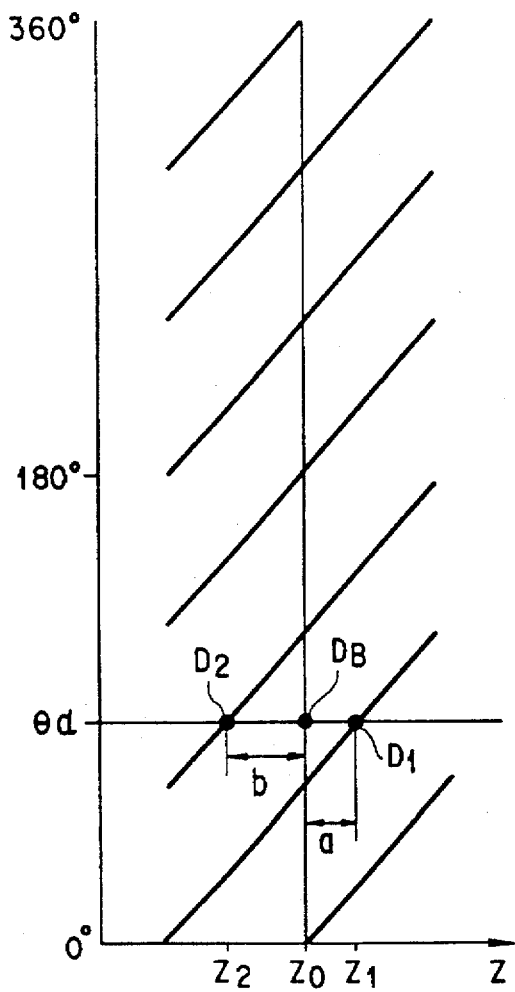
F I G. 6    $D_3 = (a \times D_1 + b \times D_2)/2$

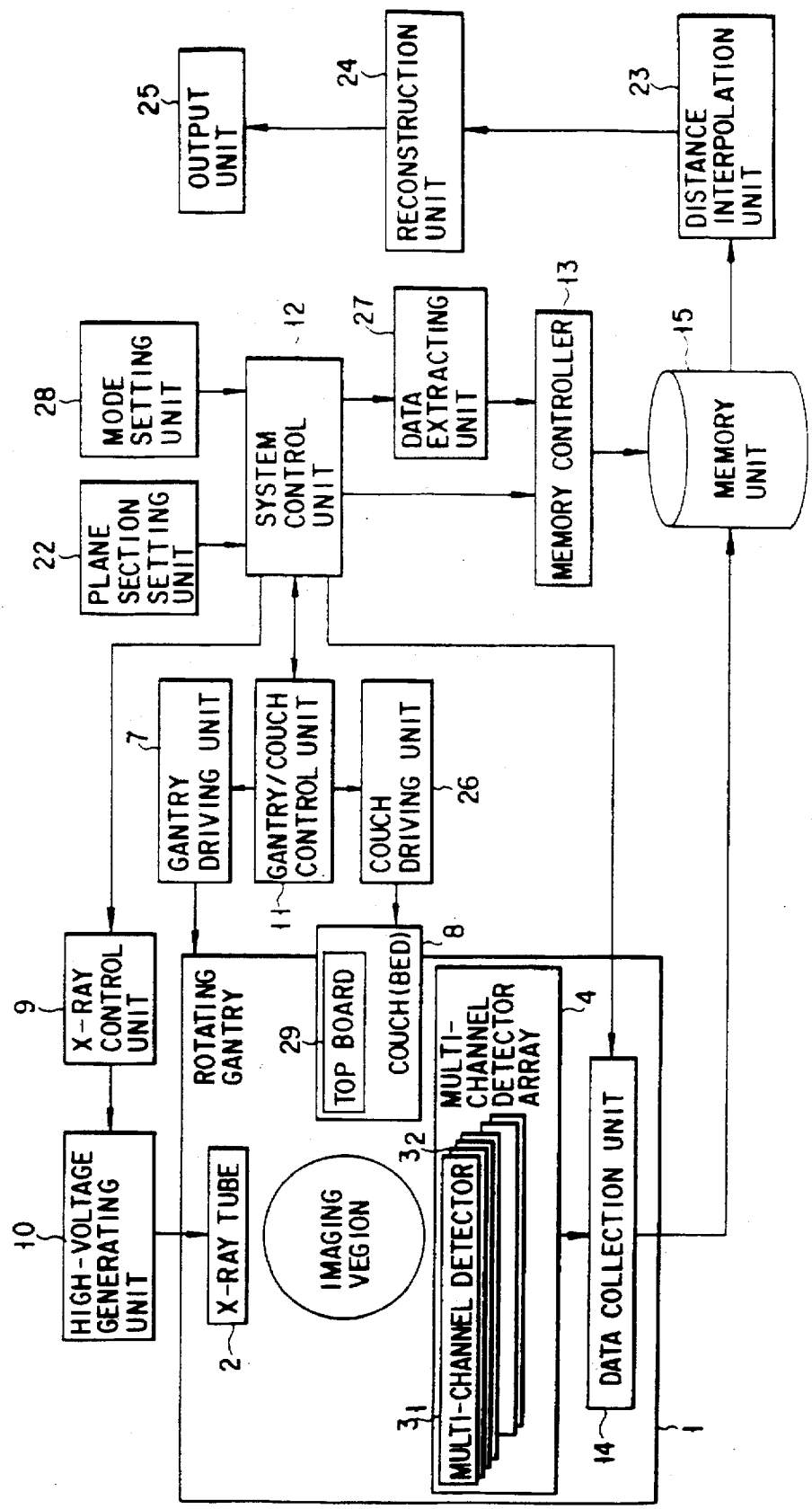
F I G. 7

X-RAY COMPUTERIZED TOMOGRAPHY APPARATUS

This is a divisional of application Ser. No. 08/352,087, filed Nov. 30, 1994 U.S. Pat. No. 5,541,971 which is a continuation-in-part of Ser. No. 08/286,423, filed Aug. 5, 1994 (abandoned).

BACKGROUND OF THE INVENTION

1. Field of the Invention

The present invention relates to an X-ray computerized tomography apparatus which reconstructs an image of a plane section of a human body under examination from X-ray signals (projection data) obtained by detecting the variation in X-ray transmission through the plane section of the body at various angles.

2. Description of the Related Art

The important problems that confronted X-ray computerized tomography apparatus since its development were the improvement in image quality and the reduction of scan time required. The helical scan, which is an epoch-making solution for these problems, is attained by combining continuous rotation of a gantry, to which an X-ray tube is mounted, around a subject under examination and continuous movement of the subject parallel to the axis of rotation of the gantry. With this helical scan, assuming the subject to be fixed, the X-ray tube will move helically along the body axis of the subject.

The helical scan has the following drawbacks. In the helical scan, the angle of the rotating gantry changes periodically (hereinafter referred simply to as the angle) and moreover projection data are acquired in each of successive locations (hereinafter referred to as the Z-axis coordinate) along the slice axis (hereinafter referred to as the Z axis) parallel to the body axis of the subject. In order to reconstruct a single tomogram of a plane section of the subject using such projection data, the simple interpolation method requires two rotations of projection data (data obtained during two rotations) with the Z-axis coordinate of the plane section taken as center. Distance interpolation is performed on two rotations of projection data to obtain one rotation of projection data. The distance interpolation is a process of taking a weighted average of two pieces of data obtained at the same angle of rotation but at different Z-axis coordinates according to their distance from the Z-axis coordinate of the plane section. A tomogram of that plane section of the human body is reconstructed from one rotation of projection data thus obtained.

Thus, in the helical scan, all-angular projection data required to reconstruct a single tomogram will be dispersed within a range of distance through which the subject (laid down on a top board) moves while the gantry makes two rotations, which will result in decreased reliability of tomograms.

Opposed beam interpolation was developed to minimize this difficulty. Data acquired in positions with an angular difference of 180 degrees therebetween principally contain information about the same tissues (X-ray absorption information). Thus, the opposed beam interpolation handles projection data acquired at an angle and at a Z-axis coordinate as projection data (hereinafter referred to as opposed data) which would be obtained at the angle differing by 180 degrees from that angle and at the same Z coordinate. With such opposed beam interpolation, projection data from all angles required to reconstruct a single tomogram will be dispersed within a range of distance through which the subject (the top board) moves while the gantry makes one rotation around the subject. In principle, therefore, the opposed beam interpolation allows the reliability of tomograms to be increased by a factor of two over the simple interpolation.

SUMMARY OF THE INVENTION

It is therefore the object of the invention to provide an X-ray computerized tomography apparatus which permits the positional dispersion of detected X-ray signals (projection data) required to reconstruct a single tomogram to be decreased to thereby increase the tomogram reliability.

According to an aspect of the present invention there is provided an X-ray computerized tomography apparatus comprising: a rotating gantry to which an X-ray source is mounted; n number of X-ray detector arrays (n is an integer of two or more) which are opposed to the X-ray source with an imaging region of a subject under examination interposed therebetween, each of the X-ray detector arrays comprising a one-dimensional array of a plurality of X-ray detector elements for detecting X-rays transmitted through the subject under examination, and the X-ray detector arrays being disposed in parallel with one another at a predetermined pitch; rotating gantry driving means for driving the gantry to rotate around the imaging region; X-ray source driving means for supplying power to the X-ray source to emit X-rays; a couch having a top board on which the subject under examination is laid down; top board driving means for permitting the top board to travel along the body axis of the subject under examination to thereby change the relative position of the gantry and the top board; control means for controlling the gantry driving means, the X-ray source driving means, the X-ray detector arrays, and the top board driving means to thereby permit the gantry driving means to continuously rotate the gantry around the subject under examination, the X-ray source driving means to cause the X-ray source to emit X-rays continuously or intermittently while the gantry is rotating, the X-ray detector arrays to repeatedly detect X-rays transmitted through the subject under examination while the gantry is rotating, and the top board driving means to continuously change the relative position of the gantry and the top board along the body axis of the subject while the gantry is rotating; storage means for storing X-ray signals detected by the respective X-ray detector elements of the X-ray detector arrays, each of the X-ray signals being stored associated with an angle of rotation of the gantry and the relative position of the gantry and the top board at the time it was detected, and each of X-ray signals which are the same as the X-ray signals being stored associated with an angle of rotation of the gantry differing by 180 degrees from the angle of rotation at the time of detection and the relative position of the gantry and the top board at the time of detection; setting means for setting the position of a plane section of the subject under examination to reconstruct its tomogram; selecting means for selecting a pair of X-ray signals for the same angle of rotation of the gantry for each of predetermined angles of rotation ranging from 0° to 360°, the pair of X-ray signals for the same angle of rotation comprising a first X-ray signal corresponding to a first position closest to the position of the plane section set by the setting means and a second X-ray signal corresponding to a second position closest to the position of the plane section on the opposite side of the first position for the first X-ray signal with respect to the position of the plane section; weighted-averaging means for weighted-averaging the first and second X-ray signals for the same angle of rotation selected by the selecting means according to their distance from the position of the plane section set by the setting means; reconstructing means for reconstructing a tomogram from output signals of the weighted averaging means; and output means for outputting the tomogram reconstructed by the reconstructing means.

The X-ray computerized tomography apparatus of the present invention includes n number of X-ray detector arrays (n is an integer of two or more). Each of X-ray signals detected by means of helical scan is stored associated with an angle of rotation of the gantry and the relative position of the gantry and the top board at the time it was detected. Each of the X-ray signals is also stored associated with an angle of rotation of the gantry differing by 180 degrees from that at the time of detection and the corresponding relative position of the gantry and the top board at the time of detection. By the selecting means two X-ray signals for the same angle of rotation of the gantry are selected for each of predetermined angles of rotation ranging from 0° to 360°. A first X-ray signal corresponding to a first position closest to the position of a plane section of a subject under examination and a second X-ray signal corresponding to a second position closest to the position of the plane section on the opposite side of the first position with respect to the position of the plane section are subjected to weighted-averaging. A tomogram of the plane section of the subject under examination is reconstructed from the results of the weighted-averaging. In this manner, the tomogram is reconstructed using X-ray signals detected from regions close to the plane section, which permits reliability of the tomogram to be increased.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below serve to explain the principles of the invention.

FIG. 1 is a block diagram of an X-ray computerized tomography apparatus embodying the present invention;

FIG. 5 illustrates a range of projection data and opposed data which are loaded from a memory unit so as to reconstruct a tomogram of a preselected plane section of a subject under examination;

FIG. 6 is a diagram for use in explanation of the distance interpolation method;

FIG. 7 is a diagram of a structure of an X-ray computerized tomography apparatus according to the second embodiment of the present invention;

DETAILED DESCRIPTION OF THE PREFERRED EMBODIMENT

Figure 2A:
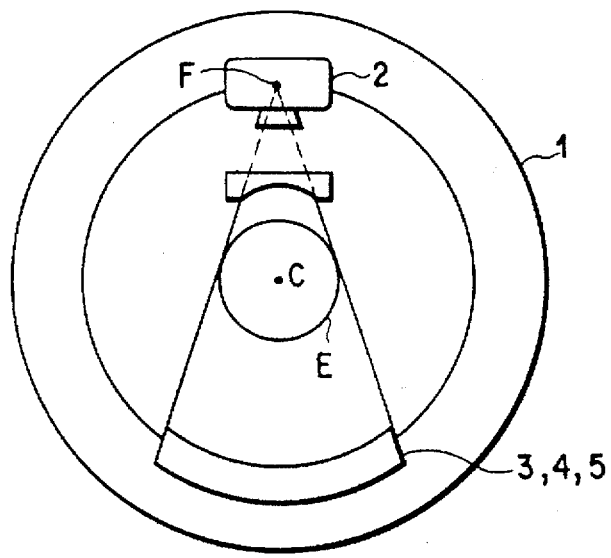
FIGS. 2A, 2B and 2C are diagrams illustrating the structural relationship between the X-ray tube and the X-ray detector arrays of FIG. 1.
Figure 2B:
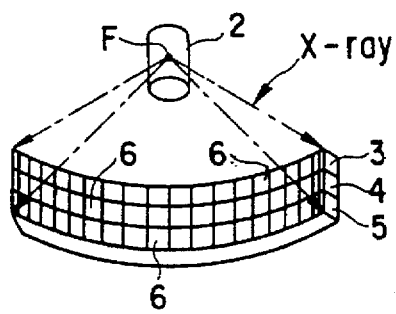
Figure 2C:
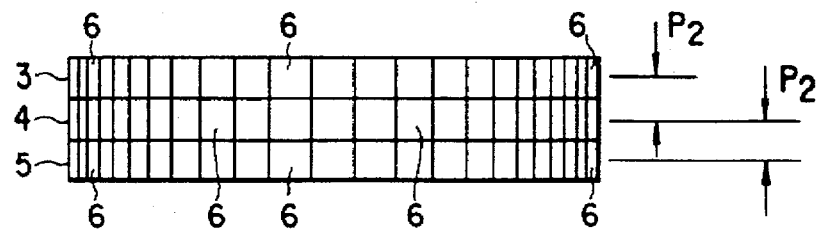

Hereinafter an embodiment of an X-ray computerized tomography apparatus of the present invention will be described with reference to the drawings. FIG. 1 is a block diagram of an X-ray computerized tomography apparatus embodying the present invention. FIG. 2A is a front view of the rotating gantry shown in FIG. 1. FIG. 2B illustrates, in perspective, the disposition of multi-channel X-ray detector arrays with respect to the X-ray tube. FIG. 2C is a front view of the multi-channel X-ray detector arrays from the X-ray tube.

The rotating gantry 1 supports an X-ray tube 2 and n number of multi-channel X-ray detector arrays (n is an integer of two or more; n=3 in this embodiment) 3, 4 and 5. The X-ray detector arrays 3, 4 and 5 are disposed to be opposed to the X-ray tube 2 with an imaging region E interposed therebetween. The X-ray tube 2 emits X-rays in the shape of a fan from its focus F. Each of the X-ray detector arrays 3, 4 and 5 comprises a plurality of X-ray detector elements 6 that are arranged one-dimensionally along the orbit of the X-ray tube 2 which rotates around the imaging region E. The multi-channel X-ray detector arrays are disposed in parallel with the center-to-center spacing, or pitch, of P2. Each of the X-ray detector elements 6 individually detects X-rays transmitted through a subject under examination and converts them into an electric signal (hereinafter referred to as an X-ray signal) the magnitude of which is proportional to the strength of the detected X-rays. There are two cases where (1) each X-ray detector element comprises one channel and (2) a predetermined number of X-ray detector elements comprise one channel. In the latter case, the detected X-ray signals from the X-ray detector elements comprising one channel are summed. The former case will be described herein for convenience of description. However, this will not intend to exclude the possibility of the latter case.

As an alternative embodiment, the rotating gantry 1 may support only the X-ray tube 2. In this case, in order to accommodate a 360-degree rotation of the X-ray tube around the center of rotation of the gantry, the X-ray detector arrays are arranged fixed along a circle having a center at the center of rotation of the gantry. However, description will be made here of the case where the X-ray tube 2 and the multi-channel X-ray detector arrays 3, 4 and 5 rotate together.

A gantry driving unit 7 drives the gantry 1 to rotate. The gantry driving unit 7 also drive the gantry 1 to move along the body axis of a subject under examination. A couch 8 is equipped with a rectangular top board on which a subject under examination is to be laid down and a slide mechanism. The slide mechanism drives the top board to slide so that the subject is allowed to have access to the imaging or photographing region E. The couch is placed so that the long side of the top board is parallel to the axis of rotation (the axis that is normal to the paper surface and aligned with the center C of rotation) of the gantry 1. As the top board slides, the subject is gradually inserted into or drawn out of the imaging region E along its body axis.

An X-ray control unit 9 provides a control signal to a high-voltage generating unit 10. A high voltage (tube voltage), the magnitude of which depends on the control signal, is applied from the high-voltage generating unit 10 to the X-ray tube 2. In response to this, the X-ray tube 2 emits X-rays the strength of which depends on the magnitude of the tube voltage.

A gantry/couch control unit 11 provides a control signal to each of the gantry driving unit 7 and the couch 8. The gantry driving unit 7 drives the gantry 1 to continuously rotate at an angular velocity specified by the control signal from the gantry/couch control unit 11. Also, the gantry driving unit 7 drives the gantry 1 to continuously slide at a speed specified by the control signal from the gantry/couch control unit 11. The couch 8 causes the top board to continuously slide at a speed specified by the control signal from the gantry/couch control unit 11. In this case, at least one of the gantry 1 and the top board is driven to slide. This permits the relative position of the gantry 1 and the top board to change. Here, the present embodiment will be described as permitting only the top board to slide.

A system control unit 12 controls the gantry/couch control unit 11, the X-ray control unit 9, and the multi-channel detector arrays 3, 4 and 5 in accordance with a predetermined sequence to thereby permit helical scan. Under the control of the system control unit 12, the gantry/couch control unit 11 permits the gantry 1 to rotate continuously. Under the control of the system control unit 12, the couch 8 permits the top board to slide continuously while the gantry 1 is rotating. While the gantry 1 is rotating, the X-ray control unit 9 permits the high-voltage generating unit 10 to apply the tube voltage to the X-ray tube 2 continuously or intermittently under the control of the system control unit 12 so that it can emit X-rays continuously or intermittently. Under the control of the system control unit 12, the multi-channel detector arrays 3, 4 and 5 repeatedly detect X-rays transmitted through the subject while the gantry 1 is rotating and the X-ray tube 2 is emitting X-rays. The X-rays undergo decay when they pass through tissues of the subject under examination. Upon detecting the X-rays which have undergone decay, each detector element of the X-ray detector arrays 3, 4 and 5 converts them into an electric signal the magnitude of which corresponds to their strength. An X-ray signal detected by each of the X-ray detector elements of the multi-channel detector arrays contains integrated information about X-ray absorption factors of the respective types of tissues through which X-rays passed, which may be called projection data.

During helical scan, the gantry/couch control unit 11 provides an angle of rotation of the gantry 1 and the coordinate of the top board (hereinafter referred to as the top board position or simply as the position) to the system control unit 12 at all times. For this purpose, the gantry driving unit 7 is equipped with sensor means, such as an encoder, for sensing the angle of rotation of the gantry 1, and the couch 8 is equipped with sensor means, such as an encoder, for sensing the top board position.

Each time the multi-channel X-ray detector arrays 3, 4 and 5 detect the X-rays that passed through the subject, the system control unit 12 provides to a memory controller 13 the angle of rotation of the gantry and the position of the top board (the Z-axis coordinate of the top board) at that time, and the channel numbers and detector array numbers associated with the respective detected X-ray signals.

The memory controller 13 generates to a storage unit 15 two write address signals for each X-ray signal. One of the address signals is generated in accordance with an output of the system control unit 12. Being generated in accordance with the output of the system control unit 12 as with the first address signal, the other address signal is generated such that the angle of rotation of the gantry 1 at the time when that X-ray signal was detected has been shifted by 180 degrees. Thus, one X-ray signal is stored in two storage locations designated by those addresses. Considering that the X-ray signal stored in one location is original data, the other X-ray signal stored in the other location is handled as opposed data for the original data.

Each of the X-ray signals from the respective detector elements of the multi-channel X-ray detector arrays 3, 4 and 5 is subjected to amplification and analog-to-digital conversion in a data collection unit 14 and then sent to the storage unit 15 individually for storage into two locations designated by two write addresses generated by the memory controller 13.

Suppose here for convenience of description that the memory unit 15 has a number n (the number of the X-ray detector arrays; three in this embodiment)×2 of memories 16 through 21. In the 1st memory 15 there are stored X-ray signals (original data) detected by the first X-ray detector array 3. In the 1'st memory are stored the X-ray signals detected by the first X-ray detector array 3 as opposed data. In the 2nd memory 18 are stored X-ray signals (original data) detected by the second X-ray detector array 4. In the 2'nd memory 19 are stored the X-ray signals detected by the second X-ray detector array 4 as opposed data. In the 3rd memory are stored X-ray signals (original data) detected by the third X-ray detector array 5. In the 3'rd memory 21 are stored the X-ray signals detected by the third X-ray detector array 5 as opposed data.

To the system control unit 12 is attached a plane section setting unit 22, such as a mouse or trackball, which allows an operator to determine the position of a plane section of a subject under examination for imaging. The system control unit 12 outputs information on X-ray signals to be read from the memory unit 15 on the basis of the position of the plane section set by the plane section setup unit 22.

In response to this information, the memory controller 31 provides read address signals to the memories 16 through 21 of the memory unit 15. Thereby, X-ray signals required to reconstruct a tomogram of the plane section are selectively read from the storage unit 15.

To be specific, a pair of X-ray signals are selected for each of predetermined angles of rotation in the range from 0 degrees to 360 degrees. For example, if the detector arrays 3, 4 and 5 perform an operation of detecting X-rays every time the gantry 1 is rotated through 2 degrees, then a pair of X-ray signals will be selected for each of angles of rotation of 0 degrees, 2 degrees, 4 degrees . . . 354 degrees, 356 degrees, and 358 degrees. The paired X-ray signals for the same angle of rotation comprise a first X-ray signal corresponding to a first position closest to the position of a plane section set by the plane section setting unit 22 and a second X-ray signal corresponding to a second position that is closest to the position of the plane section on the opposite side of the first position with the plane section interposed therebetween.

That is, the X-ray signals selectively read from the storage unit 15 are X-ray signals corresponding to positions within a range of distance corresponding to the predetermined pitch of the X-ray detector arrays 3, 4 and 5 centered at the plane section set by the plane section setting unit 22.

The X-ray signals selectively read from the storage unit 15 are sent to an interpolation unit 23, which performs distance interpolation (weighted average) on two X-ray signals for the same angle of rotation according to their distance from the position of a plane section set by the plane section setting unit 22 and produces an interpolated signal, i.e., an estimated value of an X-ray signal corresponding to the position of the plane section. This distance interpolation is repeated for each angle of rotation of the gantry in 2-degree steps, whereby interpolated signals are obtained for predetermined angles of rotation ranging from 0 to 360 degrees.

Interpolated signals are sent from the interpolation unit 23 to a reconstruction unit 24. The reconstruction unit 24, which uses successive approximation or Fourier transformation, reconstructs a two-dimensional distribution of CT values, i.e., a tomogram from the interpolated signals. The resulting tomogram is applied to an output unit 25 for visual display or storage.

Figure 3A:
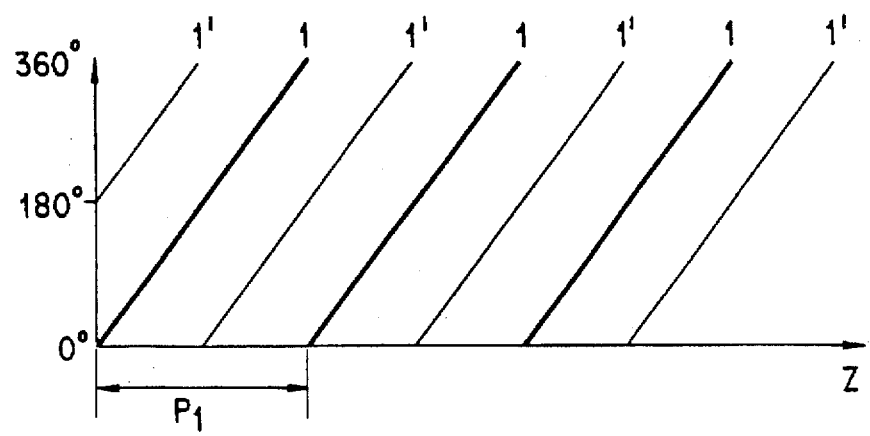
FIGS. 3A, 3B and 3C each illustrate tracks of locations where projection data are detected by a respective one of the X-ray detector arrays and tracks of locations where the opposed data corresponding to the projection data are detected.
Figure 3B:
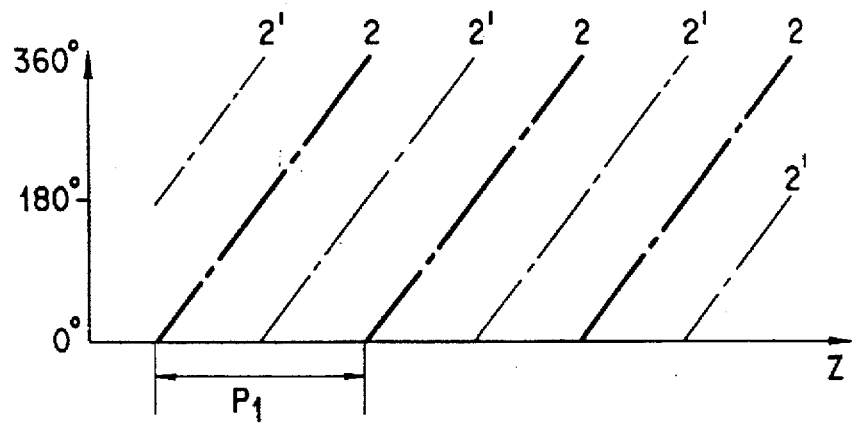
Figure 3C:
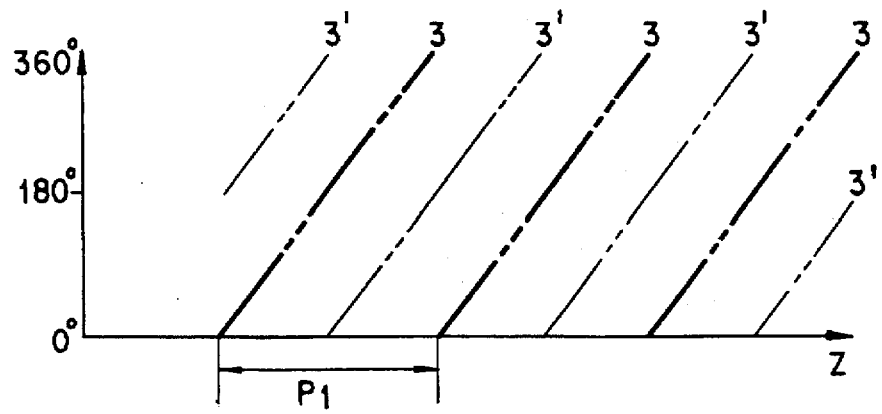

FIG. 3A illustrates positions where X-ray signals (original data detected by the first X-ray detector array 3) to be stored in the 1st memory 16 are detected and angles of rotation at the times of detection by bold lines and positions where X-ray signals to be stored in the 1'st memory 17 are detected and angles of rotation at the times of detection by thin lines. FIG. 3B illustrates positions where X-ray signals to be stored in the 2nd memory 18 are detected and angles of rotation at the times of detection by bold lines and positions where X-ray signals to be stored in the 2'nd memory 19 are detected and angles of rotation at the times of detection by thin lines. FIG. 3C illustrates positions where X-ray signals to be stored in the 3rd memory 20 are detected and angles of rotation at the times of detection by bold lines and positions where X-ray signals to be stored in the 3'rd memory 21 are detected and angles of rotation at the times of detection by thin lines.

In the present embodiment, X-ray signals are collected by helical scan. In addition, X-ray signals on a plane section of a subject under examination from all angles are prepared by means of the opposed beam interpolation method. The helical scan and the opposed beam interpolation are already known and thus they will be explained briefly here.

The helical scan is achieved by the X-ray control unit 9, the multi-channel X-ray detector arrays 3, 4 and 5, and the gantry/couch control unit 11 being controlled by the system control unit 12. More specifically, under the control of the system control unit 12, the gantry/couch control unit 11 rotates the gantry 1 continuously, and the couch 8 causes the top board to slide continuously while the gantry 1 is rotating. While the gantry 1 is rotating, the X-ray control unit 9 applies, under the control of the system control unit 12, the tube voltage to the X-ray tube 2 continuously or intermittently so as to cause the X-ray tube 2 to emit X-rays continuously or intermittently. Under the control of the system control unit 12, the multi-channel X-ray detector arrays 3, 4 and 5 detect X-rays passed through a subject under examination repeatedly while the gantry 1 is rotating and the X-ray tube 2 is emitting X-rays.

X-rays emitted from the X-ray tube 1 undergo varying degrees of decay according to types of tissues through which they pass and are detected by each detector element of the multi-channel X-ray detector arrays 3, 4 and 5.

Every time the X-ray detector arrays 3, 4 and 5 detect X-rays transmitted through a subject under examination during helical scan, the system control unit 12 provides the angle of rotation of the gantry 1 and the position of the top board (the coordinate of the top board) when each of the detector elements outputs an X-ray signal, and data on the channel numbers and detector array numbers for the respective X-ray signals from the detector arrays.

For example, at the time an X-ray signal is obtained from a channel (a detector element) in the first detector array 3, the angle of rotation $\theta a$ of the gantry 1 and the position Pa of the top board at that time are applied to the memory controller 13 together with the channel number and the detector array number associated with that channel. In response to this, the memory controller 31 provides first and second write address signals to the 1st and 1'st memories 17 and 18, respectively. In this case, the first write address signal is produced according to the angle of rotation $\theta a$, the top board position Pa, the channel number, and the detector array number. On the other hand, the second write address signal is produced according to the angle of rotation ($\theta a +$ 180°), the top board position Pa, the channel number, and the detector array number. That is, the same X-ray signal is stored in two separate locations as the original data on one hand and as the opposed data on the other hand, the locations having addresses which differ only in the angle of rotation. An X-ray signal detected at another time is also stored in the same manner. An X-ray signal on another channel is also stored in the same manner. Such is the case with individual X-ray signals of the other detector arrays 4 and 5.

Figure 4:
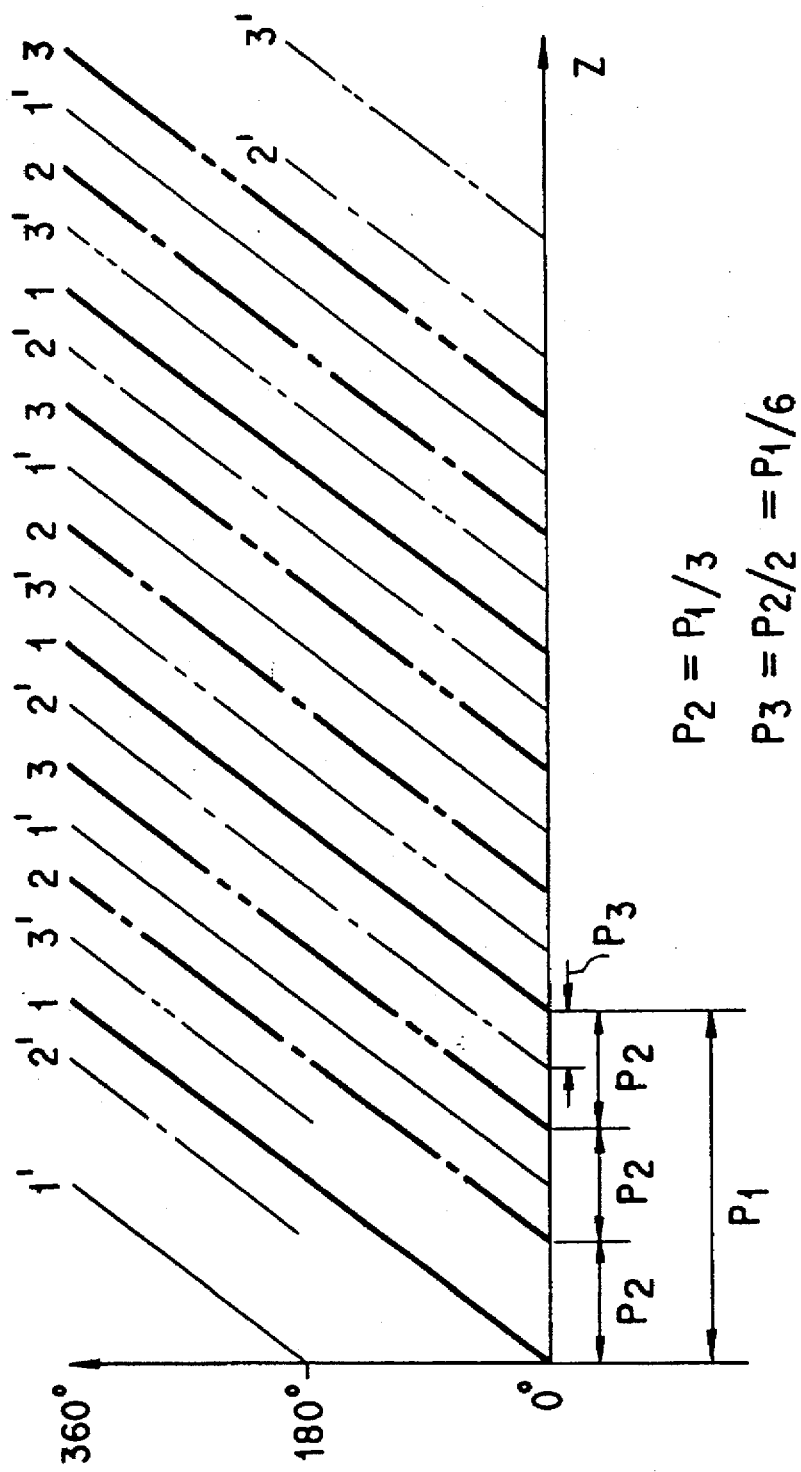
FIG. 4 illustrates tracks of locations where projection data are detected by all the X-ray detector arrays and tracks of locations where the opposed data corresponding to the projection data are detected.

FIG. 4 illustrates FIGS. 3A, 3B and 3C in combination. That is, FIG. 4 illustrates detection position versus angle of rotation for all the X-ray signals (original data) during helical scan by bold lines and that for opposed data by thin lines. In this figure, P1 indicates the distance the top board travels (top board feed pitch) while the gantry 1 makes one rotation, P2 indicates the parallel pitch of the X-ray detector arrays 3, 4 and 5, and P3 indicates the apparent parallel pitch of the X-ray detector arrays based on the opposed beam interpolation. It is one of essential factors to the present invention to make helical scan so that a string of opposed data for one detector array will be placed between strings of original data for the two other detector arrays as shown in FIG. 4. That is, it is required to narrow the positional spreading (dispersion) of detected signals required to reconstruct a tomogram for increased reliability of the tomogram. To meet this requirement, it is necessary to make helical scan under the following conditions. The conditions slightly vary between the case where an odd number of X-ray detector arrays are used and the case where an even number of X-ray detector arrays are used.

When an odd number of multi-channel X-ray detector arrays are used, the system control unit 12 controls the gantry/couch control unit 11 in such a manner as to satisfy the equation $$P1 = n \times P2 \tag{1}$$

where n=the number of the X-ray detector arrays used.

That is, the angular velocity of the rotating gantry 1 and the movement of the top board are determined by the system control unit 12 so that the distance P1 the top board travels while the gantry 1 makes one rotation around the top board may become equal to the full width (n×P2) of the detector arrays 3, 4 and 5.

When an even number of multi-channel X-ray detector arrays are used, on the other hand, the system control unit 12 controls the gantry/couch control unit 11 so as to satisfy the equation $$P1=(n-1)\times P2 \tag{2}$$

That is, the angular velocity of the rotating gantry 1 and the movement of the top board are determined by the system control unit 12 so that the distance P1 the top board travels while the gantry 1 makes one rotation around the top board may become equal to the full width (n×P2) of the detector arrays 3, 4 and 5 minus the parallel pitch P2 thereof. In this case, the orbit of the nth detector array will coincide with that of the first detector array. This makes the existence of the nth detector array insignificant. In terms of cost performance, therefore, it is preferable that an odd number of multi-channel X-ray detector arrays should be used. However, this does not means that the use of an even number of detector arrays is less effective than the use of an odd number of detector arrays.

The memory controller 13 produces two write address signals for a one-channel X-ray signal which is detected by a detector element at a time. As described above, one of the write address signals is produced in accordance with the output of the system control unit 12, while the other write address signal is produced in accordance with the output of the system control unit 12 in the same manner as the first write address signal, but in the state of having the angle of rotation of the gantry at the time When that X-ray signal was detected shifted by 180 degrees. That is, the same X-ray signal is stored in two separate locations. The same signal as the X-ray signal which is stored as original data in that location in the 1st memory 16 which is designated by an address based on the angle of rotation, the top board position, the channel number, and the detector array number is stored as opposed data in that location in the 1'st memory 17 which is designated by an address based on the angle of rotation+180°, the same top board position, the same channel number, and the same detector array number.

After the termination of helical scan or during helical scan execution, an operator enters, via the plane section setting section 22, the position of a plane section of a subject under examination for reconstructing a cross-sectional image. In response to the position of the plane section set by the plane section setting unit 22, the system control Unit 12 outputs data on a positional range of X-ray signals to be read out from the storage unit 15.

By this data, a range of distance that is equal to the parallel pitch P2 of the detector arrays 3, 4 and 5 and centered at the position of the plane section set by the plane section setting unit is specified. FIG. 5 is a diagram corresponding to FIG. 4, in which X-ray signals to be read from the storage unit 15 are indicated by bold lines. Z0 in FIG. 5 indicates the position of the plane section which has been set by the plane section setting unit 22.

That is, all the X-ray signals collected within a range of distance corresponding to the parallel pitch P2 of the detector arrays and centered at the position of the plane section set by the plane section setting unit are read from the storage unit 15. As described above, the helical scan is made so that a string of opposed data for one detector array is placed between strings of original data for the two other detector arrays. Thus, the selected X-ray signals will be read in accordance with the following rules.

That is, a pair of X-ray signals are selected for each of predetermined angles of rotation of the gantry in the range from 0° to 360°. For example, if the detector arrays 3, 4 and 5 performs an X-ray detecting operation each time the gantry 1 rotates through 2°, then a pair of X-ray signals will be selected for each of angles of rotation, 0°, 2°, 4°, ... 356°, and 358°. The two X-ray signals for each angle of rotation comprise a first X-ray signal corresponding to the first position (for example, $\overline{PO1}$) closest to the position of the plane section set by the plane section setting unit and a second X-ray signal corresponding to the second position ($\overline{PO2}$) closest to the position of the plane section on the opposite side of the first position for the first detected signal with the position of the plane section interposed therebetween. In other words, the first X-ray signal corresponding to the first position closest to the position of a plane section of a subject under examination and the second X-ray signal corresponding to the second position that is closest to the position of the plane section on the opposite side of the first position for the first X-ray signal with respect to the position of the plane section are elected for each of angles of rotation 0°, 2°, 4°, ... 354°, 356°, and 358°.

The X-ray signals thus selectively read out of the storage unit 15 are sent to the interpolation unit 23. The interpolation unit 23 performs distance interpolation (weighted average) on two X-ray signals for the same angle of rotation according to their distance from the position of the plane section set by the plane section setting unit 22 and produces an interpolated signal, i.e., an estimated value of a detected signal on the plane section.

FIG. 6 is a diagram for use in explanation of the interpolation and illustrates only the bold-line portion of FIG. 5. From two X-ray signals D1 and D2 for the same angle of rotation, say, θα, an X-ray signal D3 on the plane section (Z0) for θα is calculated in accordance with the equation $$D3=(a\times D1+b\times D2)/2 \tag{3}$$

where a indicates the distance between the position Z1 for D1 and the position Z0 of the plane section and b indicates the distance between the position Z2 for D2 and the position Z0 of the plane section.

The distance interpolation is repeated for each of predetermined angles of rotation, so that interpolated signals are obtained for the respective predetermined angles of rotation of the gantry.

The interpolated signals are sent to the reconstruction unit 24, which reconstructs the two-dimensional distribution of CT values, i.e., the image of the plane section from the interpolated signals by means of successive approximation or Fourier transformation. The cross-sectional image is sent to the output unit for visual display or storage.

Thus, according to the present invention, the positional spreading (dispersion) of detected signals required to reconstruct a cross-sectional image of a subject under examination can be made narrower than that in the prior art using a single detector array, thereby permitting reliability of the cross-sectional image to be increased. In the prior art, the spreading corresponds to the distance, P1×2, the top board travels while the gantry makes one rotation around the top board. Even if the opposed data interpolation method is adopted, the spreading will correspond to P1. In contrast, the spreading in the present invention corresponds to P2, or the parallel pitch of the detector arrays. P2 corresponds to P1/n (n is the number of the detector arrays).

The second embodiment will now be described with reference to drawings. FIG. 7 is a diagram showing the structure of the second embodiment. Those structural elements shown in FIG. 7 which are similar to those of FIG. 1 will be designated by the same reference numerals, and detailed explanations therefor will not be repeated. In this embodiment, data of a significant slice thickness similar to that of the first embodiment or less is realized from the original data only (without using the opposed data) so as to solve the problem of generating image noise caused while using opposed data.

A rotating gantry 1 supports an X-ray tube 2 and a multi-channel detector array 4 consisting of n number of arrays (n=10 in this embodiment) of multi-channel detectors 31, 32, ... 3n, such that the tube and array are arranged to oppose each other with an imaging region interposed therebetween. They are held rotatable with respect to the center of the imaging region while maintaining the relative arrangement. The X-ray tube 2 generates a cone-beam-shaped X-ray beam from the focal point. The multi-channel detectors 31, 32 ... 3n are arranged along an axis (slice axis or Z axis) perpendicular to the rotation surface of the X-ray tube 2 at a predetermined pitch p (to be called "detector pitch" hereinafter). The detector pitch p is defined by the distance between the centers in the width direction of each adjacent pair of the multi-channel detectors. Each of the multi-channel detectors 31, 32 ... 3n comprises a plurality of detection elements arranged within the rotation surface of the X-ray tube 2 to be at the same distance from the focal point of the X-ray tube 2. Each of the detection elements independently converts an X rays passing through a subject into an electric signal in accordance with the intensity of the X rays. One detection element or a predetermined number of detection elements adjacent to each other, for example, corresponds to 1 channel. This embodiment may have the so-called fourth generation structure in which only the X-ray tube 2 is held onto the rotating gantry 1, and the multi-channel detecter array 4 corresponding to one rotation is fixed to the position where it can be exposed to X rays from the X-ray tube 2.

A gantry driving unit 7 drives the rotating gantry 1 to rotate. A couch 8 supports a top board 29 on which a subject placed, to be slidable in the longitudinal direction. A couch driving unit 26 drives the top board 29 to slide, and therefore the subject is moved into or out of the imaging region along the axial direction of the subject (same as the longitudinal direction of the top board 29). With such movement, the relative position of the subject with respect to the imaging region varies. It is also possible to fix the top board 29 and slide the gantry 1 in the axial direction of the subject or move the top board 29 and the gantry 1 in the opposite direction from each other, so as to achieve a mechanism in which a positional relationship between the imaging region and the subject may vary.

The X-ray control unit 9 outputs a control signal to a high-voltage generating unit 10. A high voltage in accordance with this control signal is applied from the high-voltage generating unit 10 to the X-ray tube 2 as a tube voltage. X rays having an energy level corresponding to the tube voltage are generated by the X-ray tube 2.

A gantry/couch control unit 11 sends a control signal to each of the gantry driving unit 7 and the couch driving unit 26. The gantry driving unit 7 rotates the rotating gantry at a constant speed in accordance with the angular velocity instructed by the control signal supplied from the gantry/couch control unit 11. The couch driving unit 26 slides the top board 29 of the couch 8 at a constant speed in accordance with the control signal supplied from the gantry/couch driving unit 11. It should be noted that the top board transfer pitch d is defined as the distance in which the top board 29 slides while the rotating gantry 1, or the X-ray source 2, rotates one time.

The system control unit 12 controls the gantry/couch control unit 11, the X-ray control unit 9, the multi-channel detector array 4, and the data collection unit 14, so as to execute the helical scan. The gantry/couch control unit 11 controlled by system control unit 12 continuously rotates the rotating gantry 1 at a constant angular speed, and the top board 29 of the couch 8 is slid at a constant speed. During the rotation, the X-ray control unit 9 controlled by the system control unit 12 causes the X-ray tube 2 to generate an X rays continuously or intermittently. Each of the detection elements of the multi-channel detector array 4 controlled by the system control unit 12 converts an X rays passing through a subject into an electric signal having a level corresponding to the intensity of the X ray repeatedly at a predetermined period (for example, the time in which the X-ray tube 2 is rotated by 2° is set as one period), and the signal is output to the data collection unit 14. The data collection unit 14 controlled by the system control unit 12 converts electric signals converted by the channels of the multi-channel detector array 4 successively into digital data.

During the execution of the helical scan, the rotation angle of the rotating gantry 1 and the coordinates (position) of the top board 29 are supplied from the gantry/couch control unit 11 to the system control unit 12. For this reason, the gantry driving unit 7 is provided with a rotary encoder (not shown which generates a pulse signal for every predetermined angle, and the gantry/couch control unit 11 counts these signals so as to measure the rotation angle. Similarly, the top board 29 is provided with a rotary encoder (not shown) by means of a rack pinion mechanism which generates a pulse signal each time the top board 29 slides a predetermined distance, and the gantry/couch unit 11 counts pulse signals so as to measure the position of the top board.

The system control unit 12 outputs the rotation angle of rotating gantry 1 at a timing in which the multi-channel detector array 4 detects transmitted X rays, the position of the top board 29, the channel number of each detected data item, and a detector number unique to each of the multi-channel X-ray detectors 31 to 3n, to the memory controller 13. The memory controller 13 creates a write address signal on the basis of the rotation angle from the system control unit 12, the position of the top board 29, the channel number and the detection number, and the created signal is output to the memory unit 15. The detection data items converted into digital signals are individually transferred to the memory unit 15, and stored at respective addresses in accordance with the write address signal output from the memory controller 13. These addresses are designed for the case where the simple interpolation method is applied.

A plane section setting unit 22 for designating the position (slice position or Z-position (Z coordinate)i of a tomographic image desired by the operator is connected to the system control unit 12. The system control unit 12 supplies the data of the position of the plane section set by the plane section setup unit 22, as well as a data reading instruction, to the memory controller 13. In accordance with the data, the memory controller 13 creates a read address signal and supplies the signal to the memory unit 15. With the read address signal, the necessary data items for reconstruction of a tomogram, concerning the position of the plane section are selectively read out. More specifically, two data items are read out for every small angle of rotation over 0° to 360° (each time the gantry rotates by a small angle in a range of 0° to 360°). In other words, two data items are read out for one rotation angle. One of the two data items corresponds to the Z position closest to the position of the plane section in a positive-side region of the reconstructed tomogram region with respect to the Z axis, and the other corresponds to the Z position closest to the position of the plane section in a negative-side region of the plane section region with respect to the Z axis.

The above is the condition for the case where only a so-called interpolation (estimation when the Z position of the interpolation data is interposed between the Z positions of two original data) is used. However, as an alternative example, in the case where an extrapolation estimation when the Z position of the interpolation data is not interposed between the Z positions of two original data) is used along with the interpolation, the data item closest to the plane section position is selected as one of the two data items, and the data item second closest to the position is selected as the other of the two data items.

The data items read out in the unit of two from the memory unit 15 for every rotation angle are input to the distance interpolation unit 23. The two data items corresponding to the same rotation angle are multiplied by two coefficients (the sum of the two coefficients is 1) each determined based on the distance from the respective position of the plane section, and the multiplied data items are added together. Thus, the weighted mean data (interpolation data) of the rotation angle with regard to the position of the plane section, is formed. The formation of the interpolation data is carried out for every rotation angle, and the weighted mean data for each and every rotation angle is calculated in the end.

Based on every weighted mean data for every angle, a two dimensional distribution (tomogram) of the CT value with regard to the reconstructed tomogram, is reconstructed by an appropriate reconstruction processing method in the reconstruction unit 24. The image data of the tomogram is displayed or stored in the output unit 25.

Figure 8:
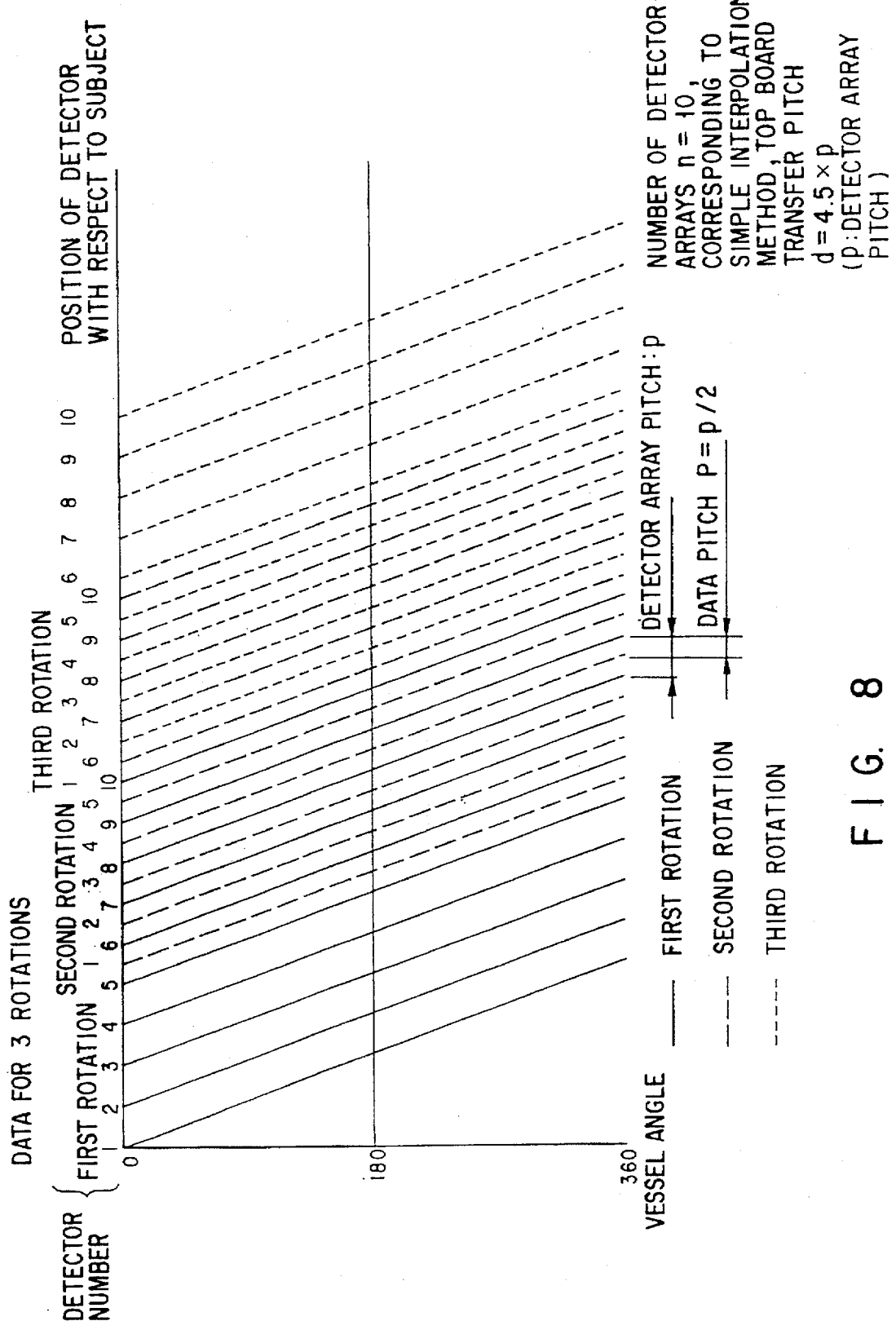
FIG. 8 is a diagram illustrating tracks of locations where projection data is detected while a subject is rotated three times under the first condition.
Figure 9:
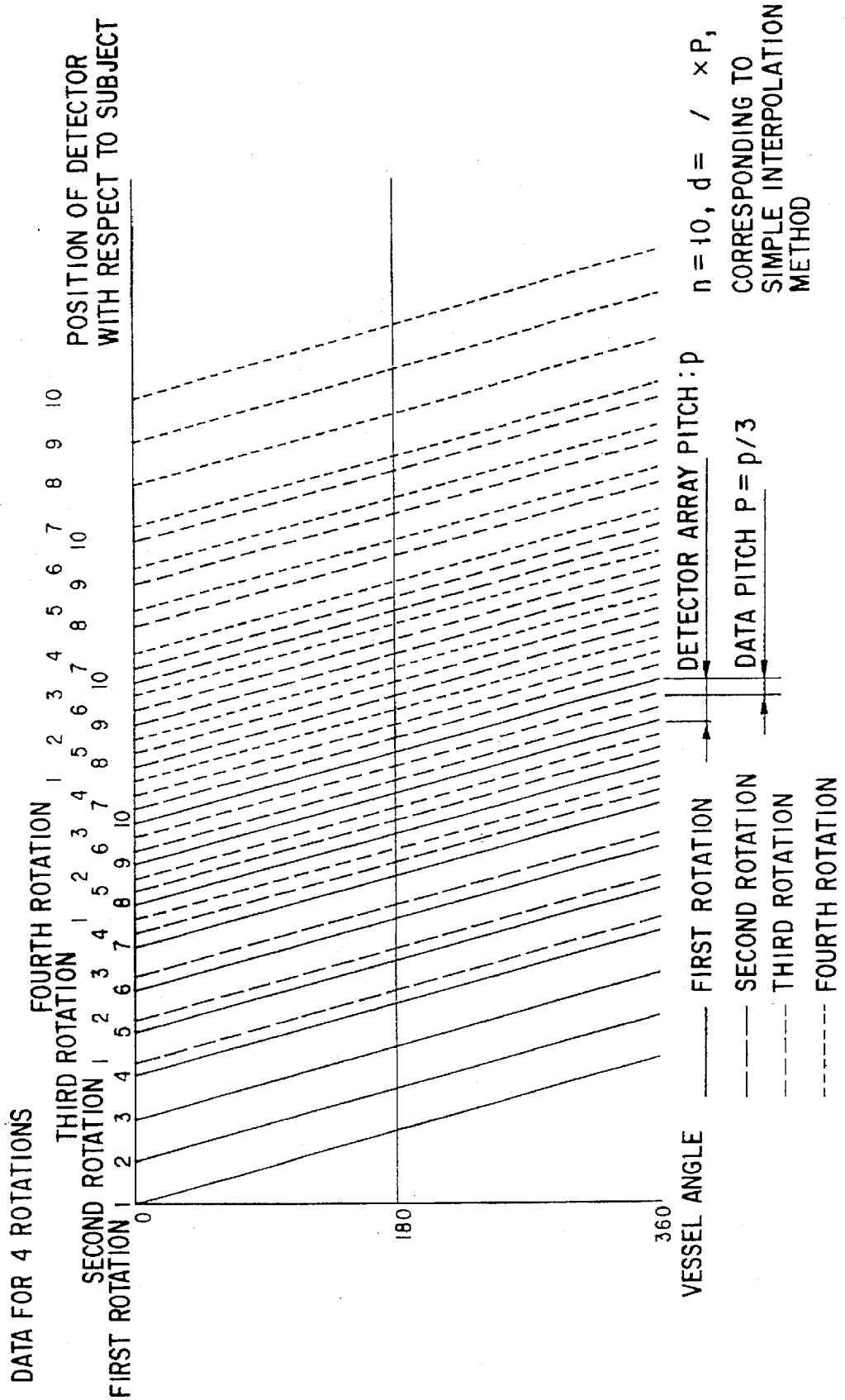
FIG. 9 is a diagram illustrating tracks of locations where projection data is detected while a subject is rotated three times under the second condition.

The operation of the embodiment will be described. In the embodiment, the number of arrays of multi-channel detectors 31-3$n$ is set to 10, i.e. n=10. FIGS. 8 and 9 each illustrate tracks of projection data collected by each of the multi-channel detectors 31-310 while the rotating gantry 1 is rotated three times, i.e. tracks expressed by the Z position of the top board 29 and the rotation angle of the rotating gantry 1 at which each data item is collected. FIGS. 8 and 9 differ from each other in the set mode of the top board transfer pitch d. Either one of the modes is selected by the operator via the mode setting unit 28 connected to the system control unit 12. In the case where the distance with regard to the Z axis between the centers in the width direction of multi-channel detectors adjacent to each other, (that is, detector pitch) is set to p, and the distance of the movement of the top board 29 while the rotation gantry 1 (X-ray tube 2) is rotated one time (that is, the top board transfer pitch) is set to d, FIG. 8 illustrates an example where d=4.5×p, whereas FIG. 9 illustrates d=(10/3)×p.

In either one of the set modes, the Z position of the data is shifted by p/2 in the set mode of FIG. 8 or by p/3 in the set mode of FIG. 9 while the rotating gantry 1 is rotated one time. Further, while the gantry 1 is rotated a plurality of times, the top board transfer pitch d is set such that the data tracks of the multi-channel detectors 31-310 overlap with each other. Consequently, the density of original data items (not opposed data items but real data items actually collected), which is the source of the weighted mean data at the position of the plane section of reconstruction, can be increased. Therefore, the image noise can be reduced by creating the weighted mean data only from the original data without using opposed data. Further, the significant slice thickness is decreased by narrowing the pitch p, making it possible to achieve an image having a high spatial resolution in the subject's axis direction.

In the case of FIG. 8, 10 arrays (n=1) of multi-channel detectors 31-310 are arranged and the top board 29 is slid at a top board transfer pitch (d=4.5×p), which is 4.5 times as much as the detector pitch p. Thus, the data pitch P can be set to p/2. Alternatively, 10 arrays (n=10) of multi-channel detectors 31-310 are arranged, and the top board 29 is slid at a top board transfer pitch (d=(10/3)×p), which is 10/3 times as much as the detector pitch p. Thus, the data pitch P can be set to p/3.

Figure 10:
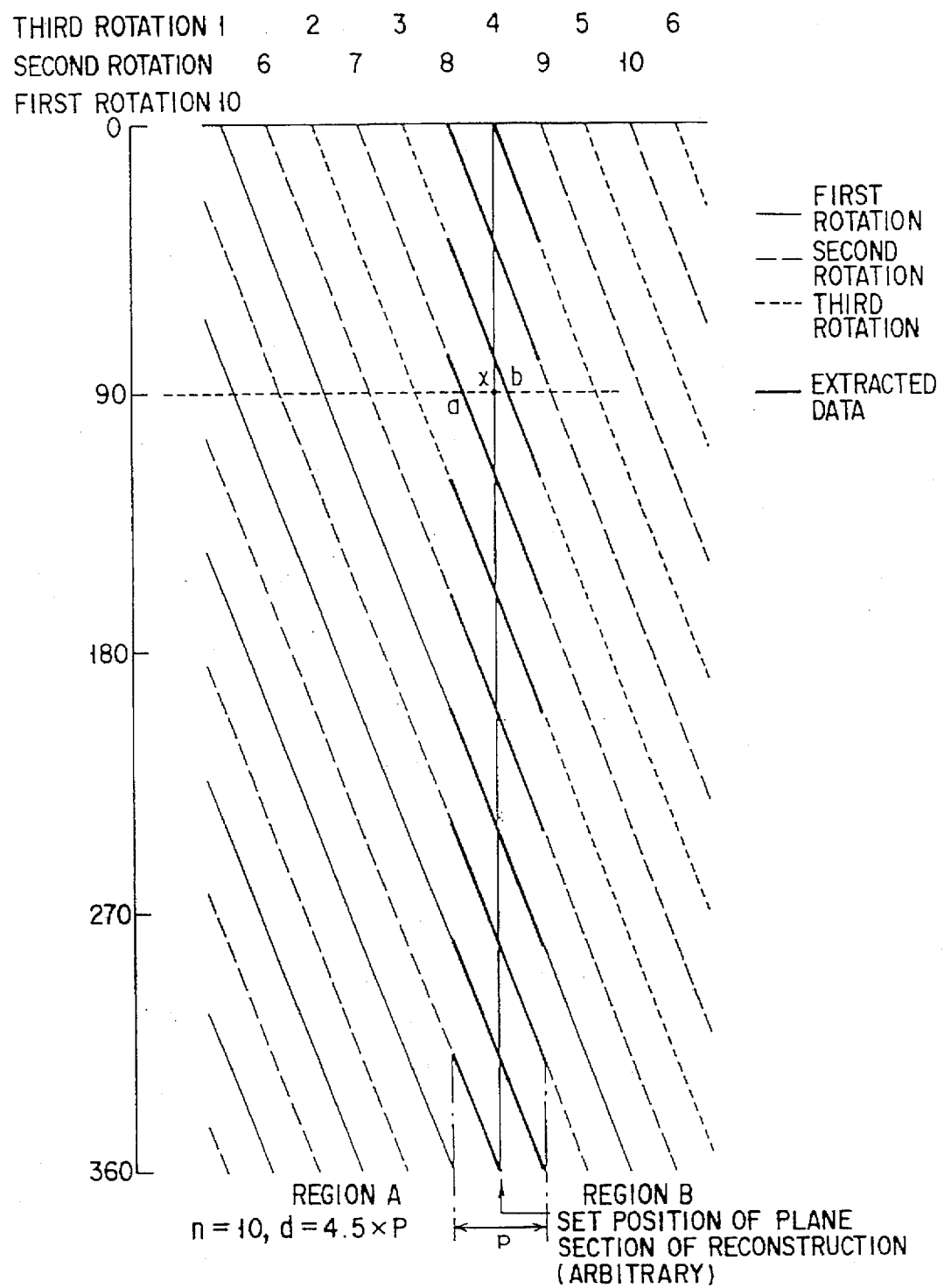
FIG. 10 is a diagram showing the significant slice thickness in the second embodiment.

FIG. 10 shows data extracted from the memory unit 15 for reconstruction in the case of FIG. 8. As shown above, rather than the opposed beam interpolation method, the simple interpolation method is employed. Let us suppose that weighted mean data corresponding to a rotation angle of, for example, 90° is obtained with respect to the position of the plane position for reconstruction set by the operator through the plane section setup unit 22. Two projection data items, which are original data items of the weighted mean data for a rotation angle of 90° are: data item a closest to the position of the plane section of reconstruction in the region A located on the left-hand side of the position of the plane section (data for a rotation angle of 90° obtained in the second rotation of the seventh multi-channel detector 37), and data item b closest to the position of the plane section of reconstruction in the region 3 located on the right-hand side of the position of the plane section (data for a rotation angle of 90° obtained in the third rotation of the third multi-channel detector 33). From these data items a and b, a weighted average data x for a rotation angle of 90° at the position of the plane section can be obtained by the distance interpolation. When such a process is carried out for every rotation angle at the position of the plane section, the data (interpolation data or weighted mean data) of all angles necessary for the reconstruction process at the position of the plane section are prepared. More specifically, the original data is present in the section indicated by bold lines, and can be limited (narrowed) to a range of −p/2 to p/2 with the position of the plane section being at the center, in other words, a range of p with the position of the plane section being at the center. Similarly, in the case of FIG. 9, the original data can be limited (narrowed) to a range of −p/3 to p/3 with the position of the plane section being at the center, in other words, a range of (2/3)×p with the position of the plane section being at the center.

The above description can be generalized in the following expression. The top board transfer pitch d can be represented by:

$$d = p \times (L + 1/m)$$

where p is the detector pitch n is the number of arrays of multi-channel X-ray detectors m is a natural number L is an integer less than (n/m).

When the top board transfer pitch d is arbitrarily adjusted via the mode setting unit while satisfying the above equation, the pitch P of the data can be expressed by:

P=p/m. In the case where the opposed beam interpolation is not used, but only the interpolation, which is of the simple interpolation method, is used, the projection data necessary for reconstruction can be limited to a range of (2×p)/m significant slice thickness). In the case of FIG. 8, the significant slice thickness is p, whereas in the case of FIG. 9, the significant slice thickness is (⅔)×p. When the weighted mean data is obtained from the projection data, the projection data items are all original data items actually collected, and are not opposed data items. Consequently, this embodiment can achieve an improved image noise as compared to the first embodiment, in which the significant slice thickness is reduced by the opposed beam, and therefore an image quality as good as that of the simple interpolation can be obtained. Further, the pitch of the projection data is p/m, and a significant slice thickness of the level of the first embodiment or less can be obtained.

Figure 11:
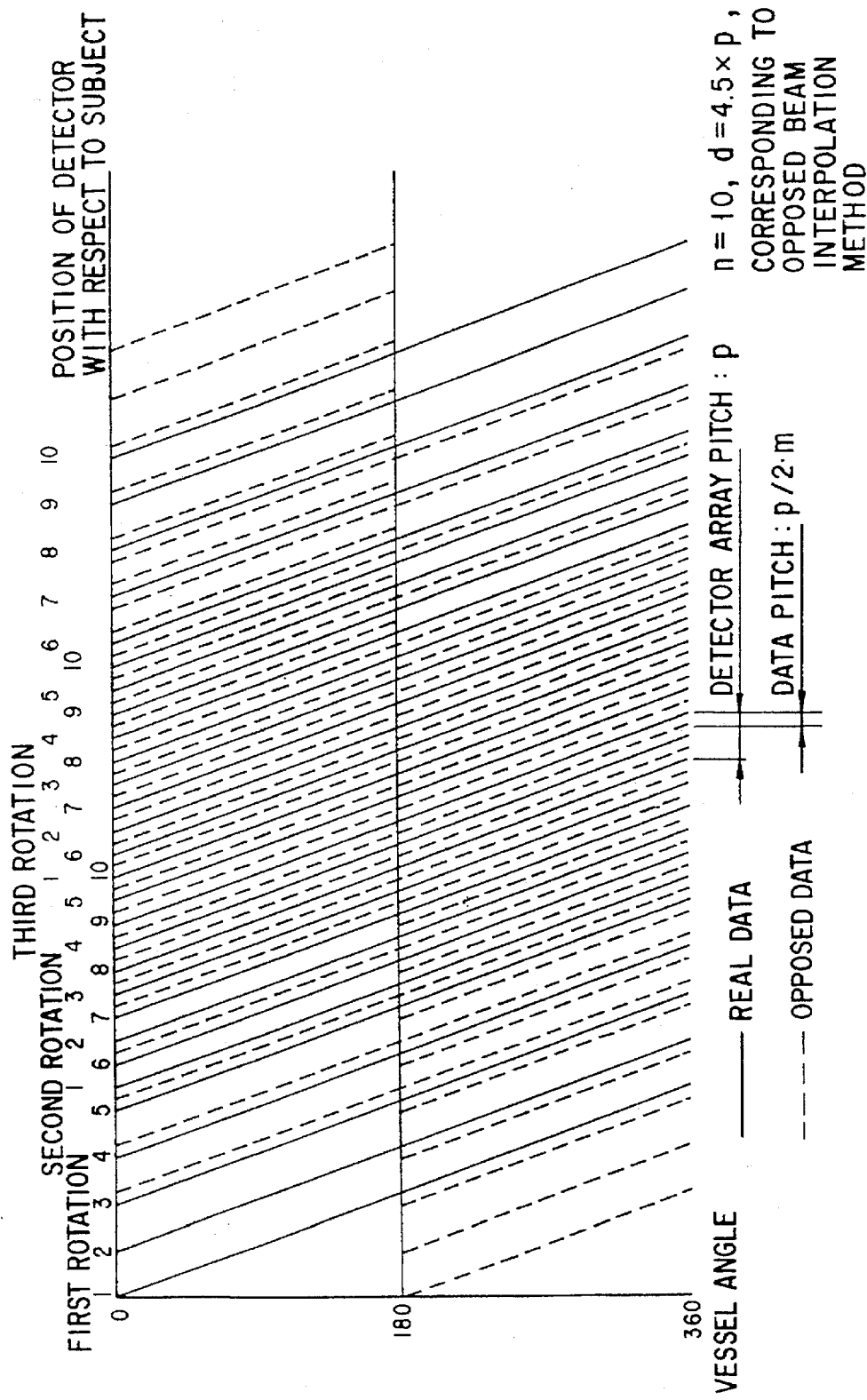
FIG. 11 is a diagram, illustrating tracks of locations where projection data and opposed data are detected while a subject is rotated three times under the first condition in The case where the second embodiment is applied to the opposed beam method.

This embodiment was described in connection with the simple interpolation method as above; however the opposed beam interpolation method can be naturally employed. For example, FIG. 11 illustrates data tracks when the opposed beam interpolation method is applied under the conditions of FIG. 8 In this case, the data pitch is p/2 m. Since one side of the projection data for calculating the weighted average data is an opposed beam, the image noise increases as compared to the case of the simple interpolation; however, with the reduction of the data pitch, the significant slice thickness can be decreased.

As described, according to this embodiment, image data (boxel data) having a less image noise, an excellent low-contrast resolution and a high spatial resolution with regard to the subject's axial direction, can be obtained at a high speed and in a short time, as the effect of the multi-slice helical scan. This is because the number of original data items whose tracks cross the plane section of reconstruction increases as compared to the first embodiment, and therefore the reconstruction can be performed by using only original data items without increasing the significant slice thickness, thus reducing the image noise.

Although the preferred embodiment of the present invention has been disclosed and described, it is apparent that other embodiments and modifications are possible.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents. For example, opposed beam interpolation may be not used.

What is claimed is:

1. An X-ray computerized tomography apparatus in which an X-ray tube for radiating an X ray and a subject irradiated with the X ray are relatively rotated with respect to each other, and the X-ray tube and the subject are relatively moved along an axial direction of the subject, thus performing a helical scan on the subject, and the X ray transmitted through the subject is detected by an X-ray detector, thus reconstructing a tomograph at a desired position of a plane section of reconstruction in the axial direction, said apparatus comprising:

multi-channel type X-ray detectors arranged in an n-number of arrays (n is an integer of 2 or more) along the axial direction of the subject;

moving means for relatively varying a positional relationship between the X-ray tube and the subject in the axial direction of the subject; and controlling means for controlling moving pitch d by which the X-ray tube and the subject are relatively moved while the X-ray tube is rotated one time so as to avoid overlapping of data tracks detected by the X-ray detectors during helical scanning, the moving pitch d satisfying the following formula:

$$d = p \times (L + 1/m)$$

wherein p is the distance between centers in a width direction of X-ray detectors adjacent to each other;
n is the number of arrays of the X-ray detectors;
m is a natural number; and
L is an integer less than (n/m).

2. An X-ray computerized tomography apparatus according to claim 1, wherein m is equal to 2 in the formula of the moving pitch d.

3. An X-ray computerized tomography apparatus comprising:

an X-ray source for irradiating a subject with X rays;
detectors arranged in an axial direction of the subject, each of said detectors having detecting elements arrayed in a direction perpendicular to the axial direction of the subject, said detectors detecting the X rays to obtain detection data when the X rays pass through the subject;

scanning means for performing scanning while the subject and said detectors move relative to one another such that said detectors move relative to the subject along present helical trajectories lacking overlap with each other and including at least one present trajectory located between at least two previous helical trajectories along which said detectors have previously moved; and producing means for producing a tomogram of a desired region of the subject based on the detection data.

4. The apparatus according to claim 3, further comprising opposite data producing means for producing opposite data obtained by shifting a rotational phase of the detection data through 180°.

5. The apparatus according to claim 4, wherein the present helical trajectories do not overlap helical trajectories associated with the opposite data having rotational phases shifted from rotational phases of the present helical trajectories through 180°.

6. The apparatus according to claim 4, wherein said opposite data producing means produces the opposite data based only on detection data obtained from detecting elements arrayed in center regions of said detectors.

7. The apparatus according to claim 3, wherein said scanning means performs the scanning such that one of said detectors moves along an associated one of the present helical trajectories lacking overlap with other trajectories along which the other detectors move.

8. The apparatus according to claim 3, wherein said producing means includes:

means for extracting from the detection data two data pieces corresponding to a region closest to the region of the subject in units of one rotation phase;
means for calculating projection data associated with the region of the subject based on the two data pieces; and
means for producing a tomogram of the region of the subject based on the projection data.

9. The apparatus according to claim 8, wherein said calculating means interpolates the projection data based on the two data pieces.

10. The apparatus according to claim 8, wherein said calculating means extrapolates the projection data based on the two data pieces.

11. The apparatus according to claim 8, wherein said extracting means includes means for producing opposite data obtained by shifting a rotational phase of the detection data through 180°, and means for extracting the two data pieces from the opposite data and the detection data.

12. The apparatus according to claim 11, wherein said calculating means interpolates the projection data based on the two data pieces extracted from the opposite data and the detection data.

13. The apparatus according to claim 11, wherein said calculating means extrapolates the projection data based on the two data pieces extracted from the opposite data and the detection data.

14. An X-ray computerized tomography apparatus comprising:

an X-ray source for irradiating a subject with X rays;

an odd number of at least three detectors arranged in an axial direction of the subject, each of said detectors having detecting elements arrayed in a direction perpendicular to the axial direction of the subject, said detectors detecting the X rays to obtain detection data when the X rays pass through the subject;

scanning means for performing helical scanning while said detectors and the subject rotate relative to one another and slide in the axial direction relative to one another such that when said detectors and the subject rotate relative to each other through 360°, said detectors and the subject slide relative to each other by a distance (P1) of an imaginary line extending along a rotational axis of said detectors and including a center of rotation of said detectors, the distance (P1) of the imaginary line being determined in accordance with a total width of said detectors measured in the axial direction of the subject; and producing means for producing, based on the detection data, a tomogram of a region of the subject located in a desired position of the subject with respect to the axial direction thereof.

15. The apparatus according to claim 14, wherein the distance (P1) of the imaginary line satisfies the following equation:

$$P1 = n \times P2$$

wherein n is a natural number and P2 is a distance between center points of any adjacent pair of said detectors.

16. An X-ray computerized tomography apparatus comprising:

an X-ray source for irradiating a subject with X rays;

an even-number of at least two detectors arranged in an axial direction of the subject, each of said detectors having detecting elements arrayed in a direction perpendicular to the axial direction of the subject, said detectors detecting X rays to obtain detection data when the X rays pass through the subject;

scanning means for performing helical scanning while said detectors and the subject rotate relative to one another and Slide in the axial direction of the subject relative to one another such that when said detectors and the subject rotate relative to each other through 360°, said detectors and the subject slide relative to each other by a distance equal to the product of an odd number and a distance (P1) of an imaginary line extending along a rotational axis of said detectors and including a center of rotation of said detectors, the distance (P1) of the imaginary line being determined in accordance with a width of each of said detectors measured in the axial direction of the subject; and producing means for producing, based on the detection data, a tomogram of a region located in a desired position with respect to the axial direction thereof.

17. The apparatus according to claim 16, wherein the distance (P1) of the imaginary line satisfies the following equation:

$$P1 = (n-1) \times P2$$

wherein P2 is a distance between centers of any adjacent pair of said detectors and n is a natural number.

18. An X-ray computerized tomography apparatus comprising:

an X-ray source for irradiating a subject with X rays;

at least two detectors arranged in an axial direction of the subject, each of said detectors having detecting elements arrayed in a direction perpendicular to the axial direction of the subject, said detectors detecting the X rays to obtain detection data when the X rays through the subject;

scanning means for performing helical scanning while said detectors and the subject rotate relative to one another and slide in the axial direction of the subject relative to one another such that when said detectors and the subject rotate relative to each other through 360°, said detectors and the subject slide relative to each other by a distance differing from a distance equal to the product of an integer and a distance of an imaginary line extending along a rotational axis of said detectors and including a center of rotation of said detectors, the distance of the imaginary line being determined in accordance with a width of each of said detectors measured in the axial direction of the subject; and producing means for producing, based on the detection data, a tomogram of a region of the subject located in a desired position of the subject with respect to the axial direction thereof.

* * * * *